(12) United States Patent
    Epshtein

(10) Patent No.: US 9,945,798 B2
(45) Date of Patent: *Apr. 17, 2018

(54) METHOD FOR DETERMINING DEGREE OF MODIFIED POTENCY OF A MEDICAMENT

(71) Applicant: Oleg Iliich Epshtein, Moscow (RU)

(72) Inventor: Oleg Iliich Epshtein, Moscow (RU)

(73) Assignee: Oleg Illiich Epshtein, Moscow (RU)

( * ) Notice: Subject to any disclaimer, the term of this patent is extended or adjusted under 35 U.S.C. 154(b) by 0 days.

This patent is subject to a terminal disclaimer.

(21) Appl. No.: 14/218,793

(22) Filed: Mar. 18, 2014

(65) Prior Publication Data

US 2014/0287448 A1    Sep. 25, 2014

(30) Foreign Application Priority Data

Mar. 18, 2013   (RU) ................................ 2013111962

(51) Int. Cl.
    *G01N 30/00*    (2006.01)
    *G01N 24/08*    (2006.01)
    *G01N 33/68*    (2006.01)

(52) U.S. Cl.
    CPC ......... *G01N 24/08* (2013.01); *G01N 33/6854* (2013.01)

(58) Field of Classification Search
    USPC .......................... 435/25; 436/547; 424/158.1
    See application file for complete search history.

(56) References Cited

U.S. PATENT DOCUMENTS

| | | | |
|---|---|---|---|
| 7,572,441 B2 | 8/2009 | Epshtein et al. | |
| 7,582,294 B2 | 9/2009 | Epshtein et al. | |
| 7,700,096 B2 | 4/2010 | Epshtein et al. | |
| 7,815,904 B2 | 10/2010 | Epshtein et al. | |
| 7,923,009 B2 | 4/2011 | Epshtein et al. | |
| 8,066,992 B2 | 11/2011 | Epshtein | |
| 8,168,182 B2 | 5/2012 | Epshtein | |
| 8,178,498 B1 | 5/2012 | Epshtein | |
| 8,241,625 B2 | 8/2012 | Epshtein et al. | |
| 8,524,229 B2 | 9/2013 | Epshtein et al. | |
| 8,535,664 B2 | 9/2013 | Epshtein et al. | |
| 8,617,555 B2 | 12/2013 | Epshtein | |
| 8,637,030 B2 | 1/2014 | Epshtein | |
| 8,637,034 B2 | 1/2014 | Epshtein | |
| 8,703,124 B2 | 4/2014 | Epshtein et al. | |
| 8,795,657 B2 | 8/2014 | Epshtein | |
| 8,815,245 B2 | 8/2014 | Epshtein | |
| 2006/0153845 A1 | 7/2006 | Epshtein et al. | |
| 2007/0123518 A1 | 5/2007 | Epshtein | |
| 2007/0141058 A1 | 6/2007 | Epshtein et al. | |
| 2008/0025985 A1 | 1/2008 | Epshtein et al. | |
| 2008/0050360 A1 | 2/2008 | Epshtein et al. | |
| 2008/0050392 A1 | 2/2008 | Epshtein et al. | |
| 2008/0131440 A1 | 6/2008 | Epshtein et al. | |
| 2009/0148521 A1 | 6/2009 | Epshtein | |
| 2010/0166762 A1 | 7/2010 | Epshtein | |
| 2010/0203059 A1 | 8/2010 | Epshtein | |
| 2010/0221258 A1 | 9/2010 | Epshtein | |
| 2010/0239569 A1 | 9/2010 | Epshtein | |
| 2011/0008452 A1 | 1/2011 | Epshtein et al. | |
| 2011/0086037 A1 | 4/2011 | Epshtein | |
| 2012/0225074 A1 | 9/2012 | Epshtein et al. | |
| 2012/0258146 A1 | 10/2012 | Epshtein | |
| 2012/0263725 A1 | 10/2012 | Epshtein et al. | |
| 2012/0263726 A1 | 10/2012 | Epshtein et al. | |
| 2012/0294899 A1 | 11/2012 | Epshtein et al. | |
| 2012/0321672 A1 | 12/2012 | Epshtein | |
| 2013/0017202 A1* | 1/2013 | Epshtein et al. ........... 424/139.1 | |
| 2013/0045237 A1 | 2/2013 | Epshtein et al. | |
| 2013/0058981 A1 | 3/2013 | Epshtein | |
| 2013/0058982 A1 | 3/2013 | Epshtein | |
| 2013/0064860 A1 | 3/2013 | Epshtein | |
| 2013/0171161 A1 | 7/2013 | Epshtein et al. | |
| 2013/0189707 A1 | 7/2013 | Epshtein et al. | |

(Continued)

FOREIGN PATENT DOCUMENTS

| | | |
|---|---|---|
| EP | 2123300 A1 | 11/2009 |
| RU | 2112976 C1 | 6/1998 |
| RU | 2161955 C1 | 1/2001 |
| RU | 2181890 C1 | 4/2002 |
| RU | 2191601 C1 | 10/2002 |
| RU | 2192888 C1 | 11/2002 |
| RU | 2195648 | * 12/2002 |
| RU | 2195648 C2 | 12/2002 |
| RU | 2438707 C2 | 1/2007 |
| RU | 2332236 C1 | 8/2008 |

OTHER PUBLICATIONS

Frimel G., "Immunological Methods", 1987, Moscow, Medicina Publishing House, pp. 9-33.

(Continued)

*Primary Examiner* — Ralph J Gitomer
(74) *Attorney, Agent, or Firm* — Pergament & Cepeda LLP; Milagros A. Cepeda; Edward D. Pergament

(57) ABSTRACT

The invention comprises a method for determining degree of modified potency of a medicament. A medicine is a medicament comprising a therapeutic component and a homeopathic, i.e., activated-potentiated, component, wherein the activated-potentiated component has some physical, chemical or biological affect on the therapeutic component and/or the pharmacological efficacy thereof. The therapeutic component is biologically related to the starting substance of the homeopathic component. An analytical measurement of at least one characteristic parameter of the therapeutic form is made prior to its interaction with the activated-potentiated form. The same analytical measurement(s) are made and after interaction between the therapeutic and activated-potentiated forms. This data is used to confirm the presence of any modified potency is caused by the presence of molecular form in the activated-potentiated form. Further, the claimed analytical measurement of at least one characteristic parameter of the therapeutic form prior to its interaction with the activated-potentiated form and again after such interaction serves to quantify the degree of modifying potency associated with the activated-potentiated form in relative dimensionless activity units (release activity).

13 Claims, 4 Drawing Sheets

(56) References Cited

U.S. PATENT DOCUMENTS

| | | | |
|---|---|---|---|
| 2013/0224219 | A1 | 8/2013 | Epshtein et al. |
| 2013/0302312 | A1 | 11/2013 | Epshtein et al. |
| 2013/0303735 | A1 | 11/2013 | Epshtein et al. |
| 2013/0315964 | A1 | 11/2013 | Epshtein et al. |
| 2013/0336985 | A1 | 12/2013 | Epshtein et al. |
| 2014/0010819 | A1 | 1/2014 | Epshtein et al. |
| 2014/0056923 | A9 | 2/2014 | Epshtein et al. |
| 2014/0079696 | A1* | 3/2014 | Epshtein .................. 424/134.1 |
| 2014/0112934 | A1 | 4/2014 | Epshtein |
| 2014/0287442 | A1* | 9/2014 | Epshtein .................... 435/7.92 |

OTHER PUBLICATIONS

Schwabe, W., "German Homeopathic Pharmacopia (Homoepathisches Arznibuch)," Stuttgart, Translatiaon of the 5th Supplement (1991) to the 1978 edition.

Grimm, et al., "Review of Electro-Assisted Methods for Water Purification," Desalination, 1998, vol. 115, pp. 285-294.

Labconco Corporation, "A Guide to Laboratory Water Purification," 2003.

Koznacheev I.A., et al., "Water Purification of Organic Inclusions in a Reverse Flow Filtration Combustion Reactor," International Journal of Heat and Mass Transfer, 2011, vol. 54, pp. 932-937.

Laffly, et al., "Monoclonal and Recombinant Antibodies, 30 Years After . . . " Human Antibodies, 2005, vol. 14, pp. 33-55.

Stewart, "The Production of High-Purity Water in the Clinical Laboratory," Laboratory Medicine, Nov. 2000, vol. 31, No. 11, pp. 605-611.

Notification of Transmittal of the International Search Report and the Written Opinion of the International Searching Authority, dated Oct. 13, 2014, for corresponding International Patent Application No. PCT/IB2014/001183.

International Search Report, dated Oct. 13, 2014, for corresponding International Patent Application No. PCT/IB2014/001183.

Written Opinion of the International Searching Authority, dated Oct. 13, 2014, for corresponding International Patent Application No. PCT/IB2014/001183.

Pavlov, I.F., et al., "Morphine and Antibodies to u-Opiate Receptors in Ultralow Doses: Effect on Oxygen Consumption," Bull Exp Biol Med, 2003, Suppl. 1, pp. 137-139.

Epshtein O.I., et al., "In Vitro Effects of Bipathic Treatment with Antibodies in Ultralow Doses during Long-Term Post-Tetanic Potentiation," Bull Exp Biol Med., 2003, Suppl. 1, pp. 111-113.

Voronina T.A., et al., "Study of Bipathic Effect of Haloperidol," Bull Exp Biol Med., 2008, vol. 145, No. 5, pp. 620-622.

\* cited by examiner

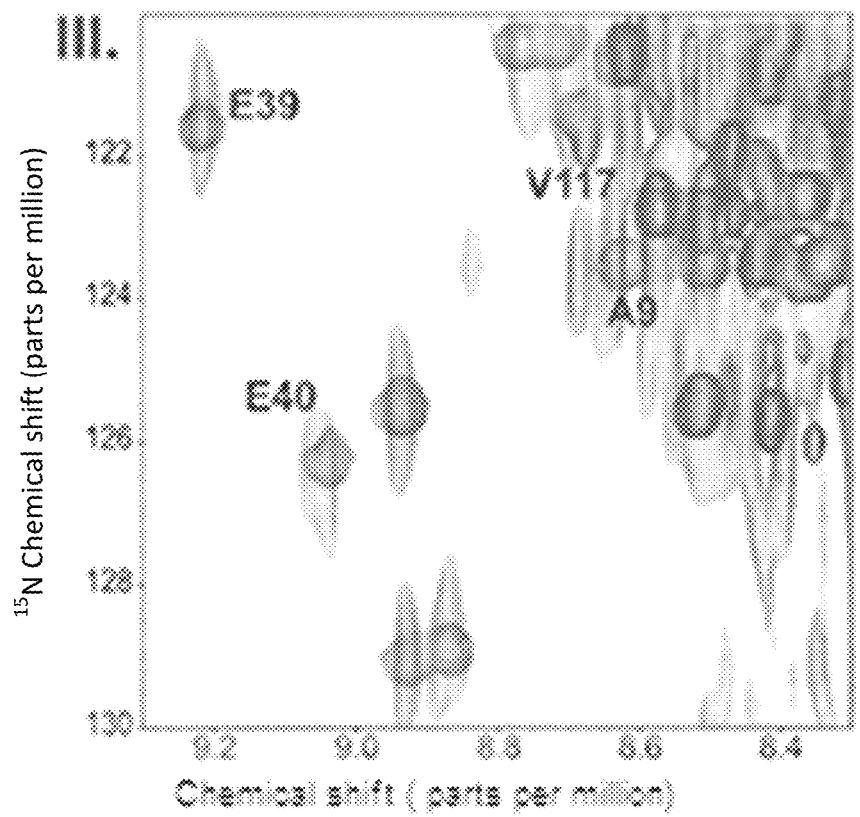
FIG. 3
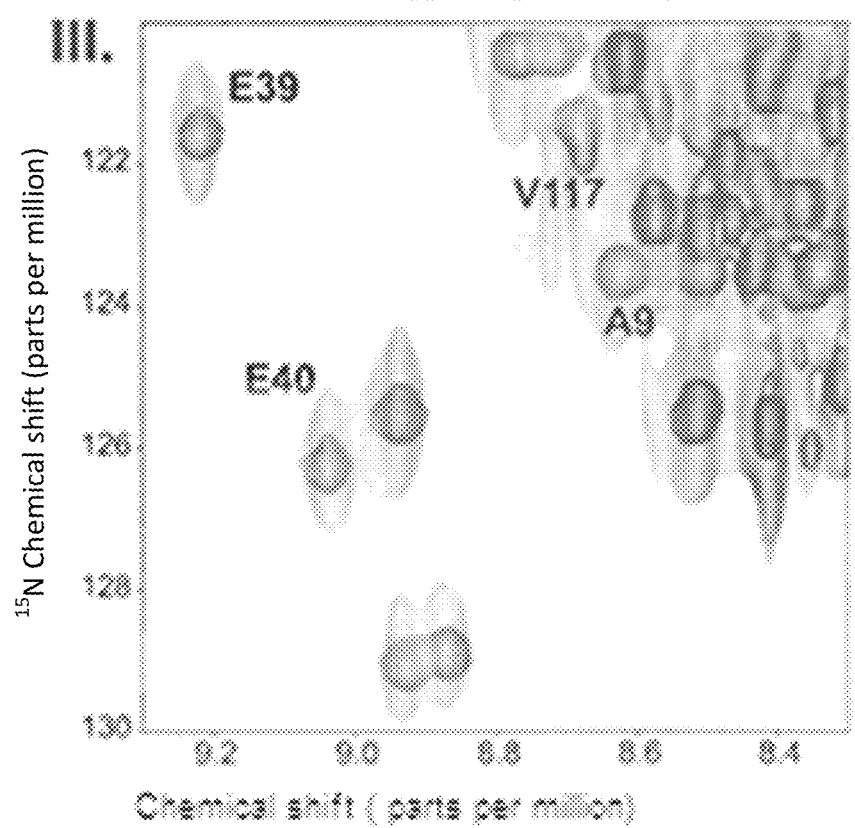

METHOD FOR DETERMINING DEGREE OF MODIFIED POTENCY OF A MEDICAMENT

This application claims priority to Russian patent application No. 2013111962, filed Mar. 18, 2013, which is hereby incorporated by reference in its entirety.

FIELD

The invention relates to the field of medicine, specifically pharmaceuticals. The invention is used for determining the modified potency of drugs, especially drugs at least one component of which is prepared according to homeopathic techniques, in a reliable and reproducible manner.

BACKGROUND

Activated-Potentiated Form

Medicaments prepared according to homeopathic techniques include those prepared by homeopathic potentiation, also referred to as activation, through multiple consecutive dilutions in a carrier (water or water-alcohol solvent)—thereby decreasing concentration—in combination with shaking of each consecutive dilution. See, e.g., RU 2191601 C1; RU 2192888 C1; RU 2332236 C1 (English version found at EP 2 123 300); and RU 2438707 C2 (U.S. Pat. Pub. 2011/0008452). The result of preparation by homeopathic potentiation is a medicament which contains low or ultra-low doses of initial medicament; dilution may proceed to approximate or exceed 1 mole of carrier per molecule of the initial medicament in molecular form, keeping in mind the total number of molecules per mole is given by Avogadro's number ($6.022 \times 10^{23}$ mol$^{-1}$). The term molecular form is further defined below. In the context of a solid, dilution is referred to as trituration. Through homeopathic techniques the carrier may acquire modifying potency, manifested in its ability to alter physical, chemical and/or biological properties of the starting substance when treated by the said activated-potentiated form (RU 2161955 C1). The activated-potentiated carrier may acquire modifying potency to alter physical, chemical and/or biological properties of a substance containing molecules similar to the structure of molecules of the starting substance when treated by said activated-potentiated form.

The term "molecular form" is used to denote one or more molecules of a particular chemical substance. Thus, the molecular form of aspirin can be a single molecule of acetylsalicylic acid; 1 mole of aspirin in molecular form consists of $6.022 \times 10^{23}$ molecules of acetylsalicylic acid and weighs 180.157 grams.

The term "activated-potentiated form" is used to denote a product of homeopathic potentiation of an initial solution containing a molecular form of a substance. In other words, a solution containing the molecular form of a substance, e.g., a specific antibody or organic molecule, is subjected to repeated consecutive dilution and multiple vertical shaking of each obtained solution in accordance with homeopathic techniques. The preferred diluent, often called the carrier, is water or a water-ethyl alcohol mixture. The preferred concentration of the molecular form in the initial carrier ranges from about 0.5 to about 5.0 mg/ml. The activated-potentiated form may be prepared from an initial solution by homeopathic potentization, preferably using the method of proportional concentration decrease by serial dilution of 1 part of each preceding solution. Thus, 1 part of the initial solution is mixed with 99 parts (for centesimal dilution) of the carrier and subjected to external impact. Preferably, the external impact involves multiple vertical shaking (dynamization) of each dilution. This results in the creation of the 1st centesimal dilution, denoted C1. The 2nd centesimal dilution (C2) is prepared by mixing 1 part of the 1st centesimal dilution C1 with 99 parts of the carrier. This procedure is repeated 10 additional times to prepare the 12th centesimal dilution C12. Separate containers are typically used for each subsequent dilution up to the required dilution factor. Similar procedures with the relevant dilution factor are performed to obtain, for example, dilutions C30, C50 and C200. This method is well-accepted in the homeopathic art. See, e.g. V. Schwabe "Homeopathic medicines", M., 1967, p. 14-29, incorporated herein by reference for the purpose stated. C12, C30, and C200 represent dilutions of the primary matrix solution (mother tincture) of antibodies $100^{12}$, $100^{30}$ and $100^{200}$ times, respectively.

Preferred activated-potentiated forms are often a mixture of several centesimal dilutions of the same molecular form. For example, a mixture of C12, C30, and C50 dilutions or C12, C30 and C200 dilutions. When using the mixture of various homeopathic dilutions each component of the composition, e.g., C12, C30, C50, C200, is prepared separately according to the above-described procedure until the next-to-last dilution is obtained, i.e., until C11, C29, and C199 respectively, and then one part of each component is added in one container according to the mixture composition and mixed with the required quantity of the carrier, i.e., 97 parts for centesimal dilution.

Examples of homeopathic potentization are described in U.S. Pat. Nos. 7,572,441 and 7,582,294, which are incorporated herein by reference in their entirety and for the purpose stated. The term "activated-potentiated form" and the term "ultra-low doses" are meant as fully supportive and primarily synonymous with one another.

Qualitative/Quantitative Assessment of Medicaments

Known in the art, e.g., RU 2181890 C1, is a method to determine the biological activity of a substance. The activity is represented by a ratio between the rate of enzymatic response to a test sample before and after adding a substance. An "optimal substance concentration in a sample" is determined in vitro. This method is not suitable, however, for determining the potency of medicaments prepared according to homeopathic techniques.

Known in the art is the method of determining homeopathic medicament potency by applying linearly polarized coherent optical radiation to an activated medicament present in a constant magnetic field. Scattered transmitted radiation is measured using time-related accumulation of values of its polarized component intensity in the mode of optical bias from different points of test medium. Analysis is conducted to calculate frequency spectrum of ultra low fluctuations of transmitted intensity and data is compared with a standard specimen. See, e.g., RU 2112976 C1.

Also known is the method for qualitative determination of homeopathic medicine or activated-potentiated form. The method includes treating a test medium with a standard specimen and registration of alterations of physical and chemical parameters. A set of known substances are used which structure and/or composition are approximately similar or similar to the ones of the determined homeopathic medicine or to the ones of potentiated substance form as well as structure and/or composition of antibodies to these known substances. Identification of homeopathic medicine or potentiated substance form shall be based on the known substance, which reaction with the appropriate antibody when homeopathic medicine or potentiated substance form are introduced into reaction medium is accompanied by alterations registered using immunochemical analytical methods based on antigen-antibody reaction (RU 2195648 C2).

The prior art methods do not, however, provide reliable and reproducible qualitative and quantitative determination of drug identity and potency associated with an activated-potentiated form. This includes activated medicaments prepared according to homeopathic techniques described above.

SUMMARY OF THE INVENTION

A method of determining activity of activated-potentiated form of a first substance, said method comprising: providing an activated-potentiated form of a first substance, assuring absence of molecular form of the substance in said activated-potentiated form, providing a molecular form of a second (therapeutic) substance structurally similar to the first substance, measuring at least one physical, chemical or biological parameter (A) of said molecular form of said second substance using a suitable analytical method, treating said molecular form of said second substance with said activated-potentiated form of said first substance, and measuring said at least one physical, chemical or biological parameter (Am) of said treated molecular form of said second substance using said analytical method, wherein said activity of said activated-potentiated form of said substance is the degree of difference between A and $A_M$.

The method described above, further comprising expressing said activity of said activated-potentiated form of said first substance in relative units (X) in accordance with the formula $X=C|A-A_M|/A$.

The method described above, further comprising i) treating a molecular form of a third substance with said activated-potentiated form of the first substance, ii) measuring said at least one physical, chemical or biological parameter (B) of said molecular form of said third substance said analytical method, iii) measuring said at least one physical, chemical or biological parameter ($B_M$) of said treated molecular form of said third substance using said analytical method to determine specificity of said method, wherein said method is considered specific when said at least one physical, chemical or biological parameter changes in statistically significant manner for $A-A_M$ and does not change in statistically significant manner for $B-B_M$.

The method described above, wherein said analytical method is High Performance Liquid Chromatography.

The method described above, wherein said analytical method is enzyme immune assay analysis.

The method described above, wherein said analytical method is Nuclear Magnetic Resonance.

The method described above, wherein said step of assuring absence of molecular form of the substance comprises removing the molecular form of said substance.

The method described above, wherein said substance is an antibody.

The method described above, wherein said antibody is a polyclonal antibody.

The method described above, wherein said substance is a small organic molecule.

The method described above, wherein said activated-potentiated form is a liquid.

The method described above, wherein said activated-potentiated form is impregnated onto a solid carrier.

The method described above, wherein said second substance is a receptor for the first substance.

The method described above, wherein said second substance is an antibody to the first substance.

The method described above, wherein said first substance is an antibody to an antigen and said second substance is a receptor for the said antigen.

The method described above, wherein said first substance is an antibody to an antigen and said second substance is the said antigen.

The method described above, wherein said first substance is an antibody to an antigen and said second substance is the said antigen.

The method described above, wherein said second substance is an enzyme catalyzed by the first substance.

BRIEF DESCRIPTION OF THE FIGURES

FIG. 3 shows alterations of chemical shift in IFN-gamma III when adding activated-potentiated carrier compared with placebo;

DETAILED DESCRIPTION OF THE INVENTION

Figure 1:
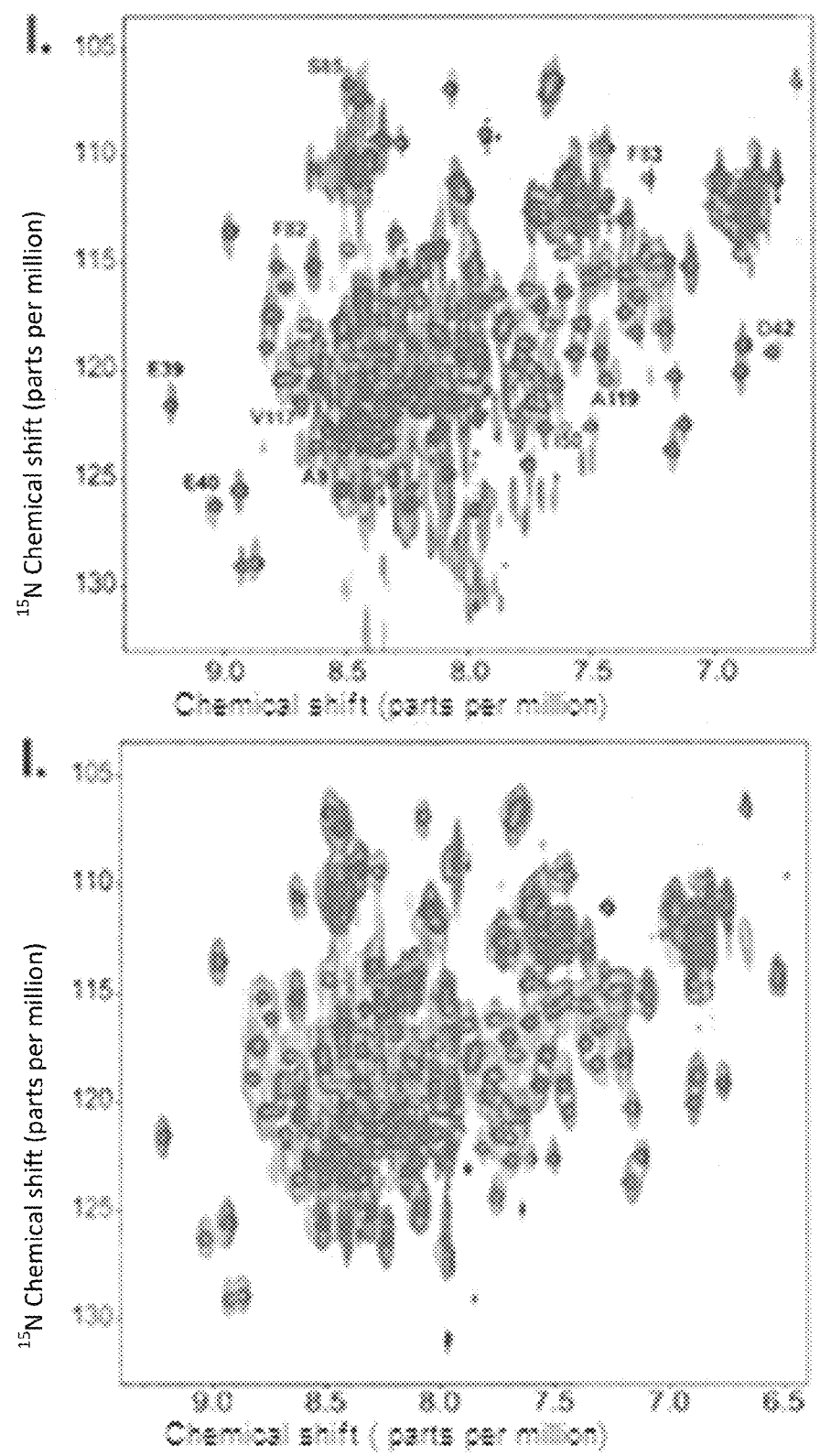
FIG. 1 shows alterations of chemical shift in IFN-gamma I when adding activated-potentiated carrier compared with placebo.
Figure 2:
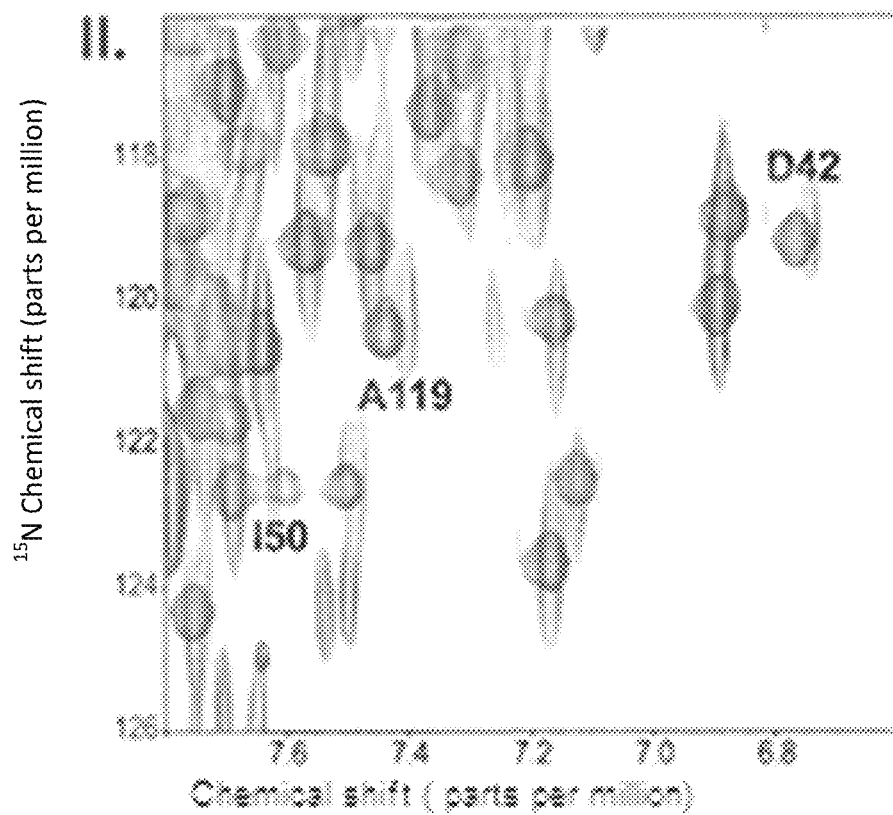
FIG. 2 shows alterations of chemical shift in IFN-gamma II when adding activated-potentiated carrier compared with placebo.
Figure 2:
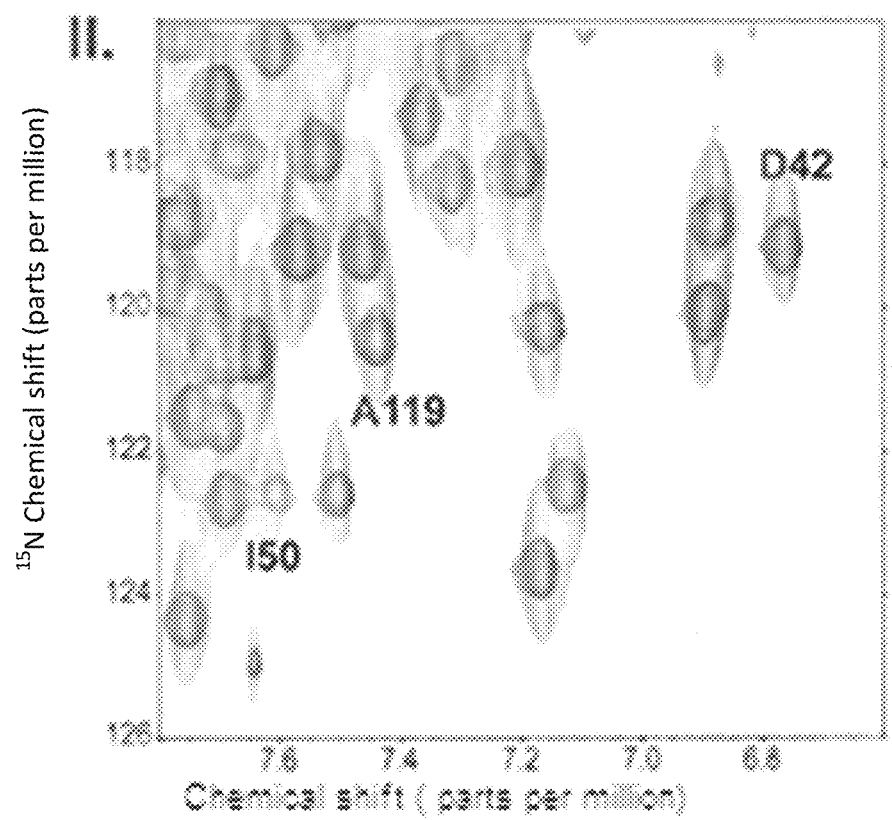

The invention is defined with reference to the appended claims. With respect to the claims, relevant definitions have been provided above and additional definitions are provided herein.

The term "antibody" as used herein shall mean an immunoglobulin that specifically binds to, and is thereby defined as complementary with, a particular spatial and polar organization of another molecule. Antibodies as recited in the claims may include a complete immunoglobulin or fragment thereof, may be natural, polyclonal or monoclonal, and may include various classes and isotypes, such as IgA, IgD, IgE, IgG1, IgG2a, IgG2b and IgG3, IgM, etc. Fragments thereof may include Fab, Fv and F(ab')$_2$, Fab', and the like. The singular "antibody" includes plural "antibodies."

The term "biologically related" with respect to a first substance and a second substance, wherein the first substance is an antibody, means that the second substance is an antigen to said first substance, a receptor of said first substance, a fragment of a receptor to said first substance, and the like. Biologically related substances are "structurally similar" as those terms are used in the present application. That is, one meaning of "structurally similar" is that the substances are biologically related. "Structurally similar" also encompasses a substance of biological or synthetic origin which interacts with the original substance, or a substance capable of interaction with the same molecules of biological or synthetic origin that are capable of interaction with the original substance.

The terms "activated-potentiated form" or "potentiated form" are used to denote a product of homeopathic potentization of any initial solution containing a molecular form of a substance, e.g., an antibody. Examples of homeopathic potentization of antibodies are described in U.S. Pat. Nos. 7,572,441 and 7,582,294, which are incorporated herein by reference in their entirety and for the purpose stated. An antibody is in the "activated-potentiated" or "potentiated" form when three factors are present. First, the "activated-potentiated" form of the antibody is a product of a preparation process well accepted in the homeopathic art. Second, the "activated-potentiated" form of antibody must have biological activity determined by methods well accepted in modern pharmacology. Third, the biological activity exhibited by the "activated-potentiated" form of the antibody cannot be explained by the presence of the molecular form of the antibody in the final product of the homeopathic process.

There has been a considerable amount of controversy regarding homeopathic treatment of human subjects. While the present invention relies on accepted homeopathic processes to obtain the "activated-potentiated" form of a substance, i.e., molecular form, it does not rely solely on homeopathy in human subjects for evidence of activity. Particular to molecular forms consisting of antibodies, it has been surprisingly discovered by the inventor of the present application and amply demonstrated in the accepted pharmacological models that the solvent ultimately obtained from consecutive multiple dilution of a starting molecular form of an antibody has definitive activity unrelated to the presence of the traces of the molecular form of the antibody in the target dilution. Also, the claimed "activated-potentiated" form of antibody encompasses only solutions or solid preparations the biological activity of which cannot be explained by the presence of the molecular form of the antibody remaining from the initial, starting solution. In other words, while it is contemplated that the "activated-potentiated" form of the antibody may contain traces of the initial molecular form of the antibody, one skilled in the art could not attribute the observed biological activity in the accepted pharmacological models to the remaining molecular form of the antibody with any degree of plausibility due to the extremely low concentrations of the molecular form of the antibody remaining after the consecutive dilutions.

While the invention is not limited by any specific theory, the biological activity of the "activated-potentiated' form of the antibodies of the present invention is not attributable to the initial molecular form of the substance. Preferred is the "activated-potentiated" form of antibody in liquid or solid carrier in which the concentration of the molecular form of the antibody is below the limit of detection of the accepted analytical techniques, such as capillary electrophoresis and High Performance Liquid Chromatography. Particularly preferred is the "activated-potentiated" form of antibody in liquid or solid form in which the concentration of the molecular form of the antibody is below the Avogadro number, i.e., 1 molecule of molecular form per $6.022 \times 10^{23}$ molecules of carrier.

The pharmaceutical composition of the invention expands the arsenal of preparations available for the treatment prophylaxis of the infectious diseases, including bacterial infections and acute and chronic viral infections.

The combination pharmaceutical composition in accordance with this aspect of the invention may be in the liquid form or in solid form. The preferred procedure for preparing the activated-potentiated component of the combination drug according to the present invention is the use of the mixture of three aqueous-alcohol dilutions of the primary matrix solution of antibodies diluted $100^{12}$, $100^{30}$ and $100^{50}$ times, respectively, which is equivalent to centesimal homeopathic dilutions C12, C30, and C50 or diluted $100^{12}$, $100^{30}$ and $100^{200}$ times, respectively, which is equivalent to centesimal homeopathic dilutions C12, C30 and C200. To prepare a solid dosage form, a solid carrier is treated with the desired dilution obtained via the homeopathic process. To obtain a solid unit dosage form of the combination of the invention, the carrier mass is impregnated with each of the dilutions. Both orders of impregnation are suitable to prepare the desired combination dosage form.

In the event that the activated-potentiated form included in the pharmaceutical composition is prepared from an antibody, it is done so in a process accepted in homeopathic art. The starting antibodies may be monoclonal, or polyclonal antibodies prepared in accordance with known processes, for example, as described in Immunotechniques, G. Frimel, M., "Meditsyna", 1987, p. 9-33; "Hum. Antibodies. Monoclonal and recombinant antibodies, 30 years after" by Laffly E., Sodoyer R.—2005—Vol. 14.—N 1-2. P. 33-55, both incorporated herein by reference.

Monoclonal antibodies may be obtained, e.g., by means of hybridoma technology. The initial stage of the process includes immunization based on the principles already developed in the course of polyclonal antisera preparation. Further stages of work involve the production of hybrid cells generating clones of antibodies with identical specificity. Their separate isolation is performed using the same methods as in the case of polyclonal antisera preparation.

Polyclonal antibodies may be obtained via active immunization of animals. For this purpose, for example, suitable animals (e.g. rabbits) receive a series of injections of the appropriate antigen (cytokine and receptor). The animals' immune system generates corresponding antibodies, which are collected from the animals in a known manner. This procedure enables preparation of a monospecific antibody-rich serum.

If desired, the serum containing antibodies may be purified, for example by using affine chromatography, fractionation by salt precipitation, or ion-exchange chromatography. The resulting purified, antibody-enriched serum may be used as a starting material for the preparation of the activated-potentiated form of the antibodies. The preferred concentration of the resulting initial solution of antibody in the solvent, preferably water or a water-ethyl alcohol mixture, ranges from about 0.5 to about 5.0 mg/ml.

An exemplary procedure for preparation of a molecular form consisting of polyclonal antibodies to CD4 receptor may be described as follows. In 7-9 days before blood sampling, 1-3 intravenous injections of the desired antigen are made to the rabbits to increase the level of polyclonal antibodies in the rabbit blood stream. Upon immunization, blood samples are taken to test the antibody level. Typically, the maximum level of immune reaction of the soluble antigen is achieved within 40 to 60 days after the first injection of the antigen. Upon completion of the first immunization cycle, rabbits have a 30-day rehabilitation period, after which re-immunization is performed with another 1-3 intravenous injections. To obtain antiserum containing the desired antibodies, the immunized rabbits' blood is collected from rabbits and placed in a 50 ml centrifuge tube. Product clots formed on the tube sides are removed with a wooden spatula, and a rod is placed into the clot in the tube center. The blood is then placed in a refrigerator for one night at the temperature of about 40° C. On the following day, the clot on the spatula is removed, and the remaining liquid is centrifuged for 10 min at 13,000 rotations per minute. Supernatant fluid is the target antiserum. The obtained antiserum is typically yellow. 20% of NaN3 (weight concentration) is added in the antiserum to a final concentration of 0.02% and stored before use in frozen state at the temperature of −20° C. or without NaN3 at the temperature of −70° C. To separate the target antibodies to gamma interferon from the antiserum, the following solid phase absorption sequence is suitable:

10 ml of the antiserum of rabbits is diluted twofold with 0.15 M NaCl, after which 6.26 g Na2SO4 is added, mixed and incubated for 12-16 hours at 4° C. The sediment is removed by centrifugation, diluted in 10 ml of phosphate buffer and dialyzed against the same buffer during one night at ambient temperature. After the sediment is removed, the solution is applied to a DEAE-cellulose column balanced by phosphate buffer. The antibody fraction is determined by measuring the optical density of the eluate at 280 nm.

The isolated crude antibodies are purified using affine chromatography method by attaching the obtained antibodies to CD4 antigen located on the insoluble matrix of the chromatography media, with subsequent elution by concentrated aqueous salt solutions.

The resulting buffer solution is used as the initial solution for the homeopathic dilution process used to prepare the activated-potentiated form of the antibodies. The preferred concentration of the initial matrix solution of the antigen-purified polyclonal rabbit antibodies to CD4 receptor is 0.5 to 5.0 mg/ml, preferably, 2.0 to 3.0 mg/ml.

Preferably, the pharmaceutical composition in the solid unit dosage form is prepared from granules of the pharmaceutically acceptable carrier which was previously saturated with the aqueous or aqueous-alcoholic dilutions of the activated-potentiated form of antibodies CD4 receptor. The solid dosage form may be in any form known in the pharmaceutical art, including a tablet, a capsule, a lozenge, and others. As an inactive pharmaceutical ingredients one can use glucose, sucrose, maltose, amylum, isomaltose, isomalt and other mono-, oligo- and polysaccharides used in manufacturing of pharmaceuticals as well as technological mixtures of the above mentioned inactive pharmaceutical ingredients with other pharmaceutically acceptable excipients, for example isomalt, crospovidone, sodium cyclamate, sodium saccharine, anhydrous citric acid etc.), including lubricants, disintegrants, binders and coloring agents. The preferred carriers are lactose and isomalt. The pharmaceutical dosage form may further include standard pharmaceutical excipients, for example, microcrystalline cellulose, magnesium stearate and citric acid.

To prepare the solid oral form, 100-300 μm granules of lactose are impregnated with aqueous or aqueous-alcoholic solutions of the activated-potentiated form of antibodies to CD4 receptor in the ratio of 1 kg of antibody solution to 5 or 10 kg of lactose (1:5 to 1:10). To effect impregnation, the lactose granules are exposed to saturation irrigation in the fluidized boiling bed in a boiling bed plant (e.g. "Hüttlin Pilotlab" by Hüttlin GmbH) with subsequent drying via heated air flow at a temperature below 40° C. The estimated quantity of the dried granules (10 to 34 weight parts) saturated with the activated-potentiated form of antibodies is placed in the mixer, and mixed with 25 to 45 weight parts of "non-saturated" pure lactose (used for the purposes of cost reduction and simplification and acceleration of the technological process without decreasing the treatment efficiency), together with 0.1 to 1 weight parts of magnesium stearate, and 3 to 10 weight parts of microcrystalline cellulose. The obtained tablet mass is uniformly mixed, and tableted by direct dry pressing (e.g., in a Korsch-XL 400 tablet press) to form 150 to 500 mg round pills, preferably, 300 mg. After tableting, 300 mg pills are obtained that are saturated with aqueous-alcohol solution (3.0-6.0 mg/pill) of the activated-potentiated form of antibodies to CD4 receptor in the form of a mixture of centesimal homeopathic dilutions C12, C30, and C50 or a mixture of centesimal homeopathic dilutions C12, C30 and C200.

Preferably, for the purpose of treatment, the combination of the invention is administered from once daily to four times daily, preferably twice daily, each administration including one or two combination unit dosage forms.

The technological result sought by the claimed invention is the increased reliability and reproducibility of methods to identify medicaments prepared according to homeopathic techniques, i.e., medicaments that do not contain the molecular form in any practically detectable concentration. Further, the claimed invention seeks increased reliability and reproducibility of methods to determine the pharmacological modifying potency associated with a medicament, i.e., an activated-potentiated form. These methods are performed in vitro, i.e., outside the body.

Methods for achieving the technological result of this invention ultimately seek to determine the degree of modifying potency associated with the activated-potentiated form which was acquired during the activation process. Processing of a starting substance containing a molecular form to achieve a medicament prepared by homeopathic techniques, i.e., the activated-potentiated form, comprises multiple consecutive dilutions with a carrier, thus decreasing the concentration of the starting substance.

The potency of the activated-potentiated form is manifested in its ability to alter or affect the physical, chemical and/or biological properties of a therapeutic dose of a different substance. The therapeutic dose contains molecules similar to the structure of molecules of the starting substance used in preparing the activated-potentiated form. The claimed invention involves determining alterations in physical parameters of the therapeutic dose utilizing analytical methods after adding thereto an activated-potentiated form of a structurally similar substance. Such analytical methods will enable determination of the presence or absence the activated-potentiated form in the therapeutic dose. The analytical methods measure one or more physical parameters of the therapeutic dose prior to and after mixing with the activated-potentiated form. The degree of potency of the therapeutic dose prior to and after mixing with the activated-potentiated form can also be measured using analytical methods. Alterations of a characteristic parameter can be provided in relative units.

Measurement of a characteristic parameter could be affected by the presence of the molecular form at detectable levels in the activated-potentiated form. If molecules of the molecular form are present at detectable levels in the activated-potentiated form, then those molecules need to be removed from the activated-potentiated form prior to mixing the activated-potentiated form and the therapeutic dose. Absence of the molecular form in a sample is, for the purposes of the present subject matter, synonymous with inability to detect said molecular form. One means of removing/rendering undetectable molecular form from an activated-potentiated form is through further dilution, e.g., homeopathic centesimal dilution. Another means is through use of a molecular sieve. A molecular sieve is a material with very small holes of precise and uniform size. These holes are small enough to block large molecules while allowing small molecules to pass. Examples of molecular sieves include activated charcoal and silica gel. Similar to a molecular sieve, any procedure and/or apparatus having a tendency to stop or even slow down the molecular form while allowing the carrier to proceed can be utilized to remove or render undetectable the molecular form. Thus, a process like high-pressure liquid chromatography ("HPLC") can be used in which the immobile phase of the HPLC apparatus stops or slows the progress of the molecular form while the mobile phase, comprising the activated-potentiated form, proceeds through the apparatus relatively unimpeded. Depending on the parameters such as affinity of the molecular form for the solid phase, the molecular form will be completely absent from the output of the HPLC apparatus for at least some known period of time.

Additionally, if molecules of the starting substance are present in the activated-potentiated carrier, they may be removed using well-established methods. In particular, the molecules of a protein taken as the starting substance may be removed, for example, by heating the activated-potentiated carrier to achieve protein denaturation followed by filtration. Alternatively, a method of desalination may be used where the protein is precipitated by high concentrations of neutral salts of alkali and alkali earth metals followed by filtration. Other possible methods include electro dialysis, deionization using ion-exchange resins; reverse osmosis; and ultra-filtration (molecular filtration) with or without preliminary filtration through larger pores. By way of further examples found in the art, refer to B. M. Steward, *The production of high-purity water in the clinical laboratory*, Laboratory Medicine, vol. 31(11), pp. 605-611 (2000); J. Grimm, D. Bessarabov, R. Sanderson, *Review of electro-assisted method for water purification*, Desalination, vol. 115 (3), pp. 285-294 (1998); I. A. Koznacheev, et al., *Water purification of organic infusions in a reverse flow filtration combustion reactor*, International Journal of Heat and Mass Transfer, Vol. 54, pp. 932-937 (1998); Labconco Corporation, *A Guide to Laboratory Water Purification*, An Industry Service Publication. http://bioresearchonline.com. Each of the foregoing publications is incorporated herein by reference for the purpose stated.

The claimed method can be realized using different methods of quantitative and qualitative determination, thus ensuring high sensitivity and reproducibility in testing the presence and potency of an activated-potentiated form. Quantitative and qualitative methods include mass spectrometry such as chromatography mass-spectrometry, gas liquid chromatography ("GLC") and high-performance liquid chromatography ("HPLC"); NMR spectroscopy, immune enzyme assay ("IEA").

Chromatography is based on partition of components of a mixture caused by the difference of their homogenous distribution between two immiscible phases. One phase in chromatography is immobile (sorbent) while another one is mobile (eluent). High pressure (up to 400 bar) and solvent slurry (generally 3-5 µm; at present it is up to 1.8 µm) are distinguishing features of HPLC. Qualitative determination using HPLC analysis is based on evaluation of retention time of chromatography peak. Quantitative determination is based on peak area evaluation Nuclear magnetic resonance spectroscopy ("NMR spectroscopy") is a research technique that exploits the magnetic properties of certain atomic nuclei. NMR determines the physical and chemical properties of atoms or the molecules in which they are contained. It relies on the phenomenon of nuclear magnetic resonance and can provide detailed information about the structure, dynamics, reaction state, and chemical environment of molecules. The intramolecular magnetic field around an atom in a molecule changes the resonance frequency, thus giving access to details of the electronic structure of a molecule. Software allows analysis of signal intensity of peaks, which under conditions of optimal relaxation, correlate with the number of protons of that type. Analysis of signal intensity is done by integration—the mathematical process that calculates the area under a curve, its size is dependent on its area.

An immune enzyme assay ("IEA") is a biochemical test that measures the presence or concentration of a macromolecule in a solution through the use of an antibody or immunoglobulin. The macromolecule detected by the immunoassay is often referred to as an "analyte". Ideally, the antibody will bind to the analyte and only the analyte. Once bound to the analyte, the antibody emits a signal indicative of the presence of a single molecule of analyte. Such a signal might be the immediate spontaneous release of a photon of light upon binding or the release of a photon of light by analyte bound antibodies upon occurrence of some 'polling' signal. Similarly, analyte bound antibodies might react differently than unbound antibodies to a later step of IEA allowing, e.g., for removal of the unbound antibodies and assessment of the number of bound antibodies remaining. Further, antibodies may be bound to a piezoelectric crystal which undergoes elastic deformation when an electrical current is applied to it. An alternating electrical current (A.C.) produces a standing wave in the crystal of a characteristic frequency. The frequency is highly dependent on the elastic properties of the crystal, which properties are affected by what is attached to the crystal. The binding of a target analyte to an antibody will produce a change in the resonance frequency, which gives a binding signal. Biological and other methods are applicable for realization of the claimed method. See, e.g., Zolotov, Yu. A. (editor), *Basics of analytical chemistry* (in 2 volumes), Textbook for universities, $3^{rd}$ edition (2004); Vasilyev, V. P., *Analytical chemistry*, (1989); Otto, M., *Up-to-date methods of analytical chemistry*, (2003).

Using a combination of analytical methods to detect the molecules of the starting substance in the said activated-potentiated carrier and measurement by analytical methods of at least one characteristic parameter of the therapeutic substance before and after its interaction with the said activated-potentiated carrier, we demonstrate (substantiate) that: first, the modifying activity associated with the carrier is not accounted for by the presence of molecules of the starting substance, and that the physical, chemical and/or biological properties of the said carrier differ from the physical, chemical and/or biological properties of the therapeutic substance; secondly, the activated-potentiated carrier is obtained by using the starting substance, where the activated-potentiated form is ensured by the very procedure employed during the technological treatment of the starting substance and represented by multiple serial concentration reduction of the latter with the use of the said carrier. Finally, based on in vitro evidence, the authenticity and identity is demonstrated for the drug product prepared using the said activated-potentiated carrier. That is, beginning with a molecular form in easily measurable concentration the activated-potentiated form is made through multiple consecutive decreasing of the concentration of the molecular form using the carrier. Further, the claimed analytical measurement of at least one characteristic parameter of the therapeutic form prior to its interaction with the activated-potentiated form and again after such interaction serves to quantify the degree of modifying potency associated with the activated-potentiated form in relative dimensionless activity units (release activity).

The degree of modifying potency pertaining to an activated-potentiated form is determined based on quantitative alterations of a characteristic parameter expressed in relative activity units (release activity), formula (1):

$$X = C|A - A_M|/A \qquad (1)$$

X is the number of activity units (AU);

C is a dimensionless constant of proportionality which is contingent on analytical methods used for measuring the characteristic parameter that reflects the initial physical, chemical and/or biological properties of the therapeutic substance and on the characteristic parameter value. In particular, for example, $C=10^k$, where k is an integer from the sequence 1, 2, 3 etc.;

A is the value of a characteristic parameter of the therapeutic substance prior to its interaction with the said activated-potentiated form (technologically treated carrier);

$A_M$ is the value of the same characteristic parameter of the therapeutic substance after its interaction with the said activated-potentiated form (technologically treated carrier).

The claimed method can be realized using different methods of quantitative and qualitative determination, thus ensuring high sensitivity and reproducibility in testing ultralow substance concentrations, such as spectrometry, particularly mass spectrometry, chromatography mass-spectrometry (gas liquid chromatography (GLC)) and high-performance liquid chromatography (HPLC) based on separation of components of a mixture caused by the difference of their homogenous distribution between two immiscible phases. One phase in chromatography is immobilized (sorbent) and the other one is mobile (eluent). High pressure (up to 400 bars) and sorbent slurry (generally 3-5 μm; here up to 1.8 μm) are distinguishing features of HPLC. Qualitative determination using HPLC analysis is based on evaluation of retention time of chromatography peak. Quantitative determination is based on peak area evaluation.

Another technique used in the realization of the claimed method is nuclear magnetic resonance spectroscopy (NMR spectroscopy) that exploits the magnetic properties of certain atomic nuclei. NMR determines the physical and chemical properties of atoms or the molecules in which they are contained. It relies on the phenomenon of resonance absorption and emission of electromagnetic energy by substances with zero-spin nuclei when placed in an external magnetic field at a frequency ν (so-called NMR frequency) which is induced by reorientation of magnetic nuclear moments, where a so-called chemical shift is the characteristic parameter. Further, the mentioned techniques include an immune enzyme assay (IEA), the use of a piezoelectric immunosensor the analytical signal of which is represented by a difference in the resonance frequency of the piezoelectric resonator (Δf) resulting from weight increases or decreases of the receptor-covered layer due to formation and destruction of immune complex on its surface. Biological and other methods are also applicable for the realization of the claimed method (e.g., see Zolotov, Yu. A. (editor), *Basics of analytical chemistry* (2 volumes), Textbook for universities, 3rd edition, revised and supplemented: Vysshaya shkola Publisher (2004); Vasilyev, V. P., *Analytical chemistry*, (1989); Otto, M., *Up-to-date methods of analytical chemistry*, (2003).

Additionally, if molecules of the starting substance are present in the activated-potentiated carrier, they may be removed using well-established methods. In particular, the molecules of a protein taken as the starting substance may be removed, for example, by heating the activated-potentiated carrier to achieve protein denaturation followed by filtration. Alternatively, a method of desalination may be used where the protein is precipitated by high concentrations of neutral salts of alkali and alkali earth metals followed by filtration. Other possible methods include electro dialysis, deionization using ion-exchange resins; reverse osmosis; and ultra-filtration (molecular filtration) with or without preliminary filtration through larger pores. By way of further examples found in the art, refer to B. M. Steward, The production of high-purity water in the clinical laboratory //Laboratory Medicine.—2000.—V. 31(11)—P. 605-611; J. Grimm, D. Bessarabov, R. Sanderson. Review of electro-assisted methods for water purification //Desalination.—1998.—V. 115 (3)—P. 285-294; I. A. Koznacheev, et al., Water purification of organic inclusions in a reverse flow filtration combustion reactor //International Journal of Heat and Mass Transfer— 1998. 54—P. 932-937; Labconco Corporation, A guide to laboratory water purification, An Industry Service Publication. Found at http://bioresearchonline.com. Each of the foregoing publications is incorporated herein by reference for the purpose stated.

Using a combination of analytical methods to detect the molecules of the starting substance in the said activated-potentiated carrier and measurement by analytical methods of at least one characteristic parameter of the therapeutic substance before and after its interaction with the said activated-potentiated carrier, we demonstrate (substantiate) that: first, the modifying activity associated with the carrier is not accounted for by the presence of molecules of the starting substance, and that the physical, chemical and/or biological properties of the said carrier differ from the physical, chemical and/or biological properties of the therapeutic substance; secondly, the activated-potentiated carrier is obtained by using the starting substance, where the activated-potentiated form is achieved through the very procedure employed during the technological treatment of the starting substance, i.e. multiple serial concentration reduction of the latter with the use of the said carrier. Finally, based on in vitro evidence, the authenticity and identity is demonstrated for the drug product prepared using the said activated-potentiated carrier.

Further, the claimed analytical measurement of at least one characteristic parameter of the therapeutic substance before and after its interaction with the activated-potentiated carrier serves to quantify the degree of modifying potency associated with the carrier in relative dimensionless activity units (release activity).

To determine the degree of modifying potency associated with the carrier, the following consecutive procedures are performed:

a. preparation of the carrier with modifying activity potentized in the course of technological processing (treatment) of the starting substance by multiple steps of serial concentration reduction using the said carrier, where the latter does not contain molecular form of the said starting substance.

b. specificity testing of the substance present in the solution from step a, which includes
   i. treatment of a molecular form of the therapeutic substance with the carrier stated in step a.)
   ii. preferably, treatment of the molecular form of a different substance and/or solvent with the carrier stated in step a.)
   iii. analytical measurement of at least one physical, chemical and/or biological characteristic parameter of the said molecular form of the therapeutic substance (A) and the said combination under paragraph b.) i.) ($A_M$), where the said carrier specifically modifies the effect-capacity to modify the physical, chemical and/or biological properties of the therapeutic substance is considered specific to the substance if the change in the said characteristic parameter with the realization of paragraph b.)i.) is statistically significant (and is not statistically significant with realization of paragraph b.)ii.))

c. determination of the modifying potency associated with the carrier in relative activity units using equation (1):

$$X = C|A - A_M|/A \quad (1)$$

X, C, A and $A_M$ are as defined previously where C is preferably equal to 100 or 1000.

EXAMPLES

The present invention is now illustrated by the following Examples, which do not limit the scope of the invention in any way.

Example 1

The purpose of Example 1 is to determine the degree of modifying potency of the activated-potentiated form of rabbit antibody ("Ab") to human interferon-gamma ("IFN-gamma"). Beginning with a mother solution of rabbit Ab to human IFN-gamma, an activated-potentiated form of rabbit Ab to human IFN-gamma was prepared by multiple consecutive dilutions decreasing of concentration of the starting substance accompanied by multiple intermediate shaking. The diluent, i.e., carrier, was a water-alcohol solution. The molecular form was diluted in $100^{12}$, $100^{30}$ and $100^{50}$ parts carrier, i.e., centesimal homeopathic dilutions C12, C30, C50. To determine alterations of physical, chemical and/or biological properties of the starting substance, i.e., rabbit Ab to human IFN-gamma, spectroscopy and nuclear magnetic resonance spectroscopy (NMR spectroscopy) were used.

As discussed above, the same atomic nuclei in different molecular environment demonstrate different NMR signals. The difference of such signal from signal of standard substance makes it possible to detect the so-called chemical shift caused by chemical composition of substance being studied, which was used as characteristic parameter reflecting information on molecular formula of a substance.

To determine conformational changes in IFN-gamma, a substance containing molecules with structure similar to rabbit Ab to human IFN-gamma affected by activated-potentiated carrier (sometimes abbreviated "AC") was added to IFN-gamma and NMR spectroscopy was applied. Release active dilutions of purified water were used as placebo.

To prepare test samples activated-potentiated form of Ab to IFN-gamma or placebo were mixed with solution of Ab to IFN-gamma in the ratio 2:1; at that final concentration of Ab to IFN-gamma in each sample was 0.8 mg/ml.

NMR experiments were performed at 25° C. on a Bruker Avance 900 MHz spectrometer, equipped with a 5 mm, triple resonance and z-axis gradient cryoprobe. AC or placebo was added to 50 μM $^{15}$N-labeled IFN-gamma solvated in 180 μl of 20 mM potassium phosphate buffer (pH 6.0) containing 20 mM NaCl and 10% $D_2O$. The spectra were acquired using a standard HSQC pulse sequence with 2048 scans in the proton dimension and 34 scans in the nitrogen dimension with a D1 delay of 1 sec. Data acquisition was carried out using Topspin Version 3.0 Software. Spectra were processed and analyzed using NMR View and Sparky software. The backbone resonances observed were assigned using previously published NMR data, acquired under similar conditions for IFN-gamma.

Alterations of chemical shift in IFN-gamma when adding AC or placebo are presented on FIG. 1 where:

On the upper row $^{15}$N—$^1$H-HSQC signals of IFN-gamma spectra in phosphate buffer (pH 6.0): in the absence of AC of Ab to IFN-gamma have spherical shape while in the presence of AC of Ab to IFN-gamma they have oval shape, full-size spectrum (from 6.5 to 9.5 parts per million) is indicated as I while regions containing strongly perturbed signals are expanded and indicated as II and III;

On the lower row $^{15}$N—$^1$H-HSQC signals of IFN-gamma spectra in phosphate buffer (pH 6.0): in the absence of placebo have spherical shape while in the presence of placebo they have oval shape, full-size spectrum (from 6.5 to 9.5 parts per million) is indicated as I while regions containing strongly perturbed signals are expanded and indicated as II and III.

Only the addition to IFN-gamma of activated-potentiated form of Ab to IFN-gamma induced pronounced alterations of chemical shift in general spectrum. On the background of adding of AC of Ab to IFN-gamma to 50 μm of IFN-gamma, alterations of chemical shift were observed for A9, E39, E40, D42, Q47, 150, F82, F83, S85, A119 and E120 residues. Besides signals corresponding to 145 and V117 residues and many undetected peaks either vanished or completely altered their position. Moreover heterogeneous signal at the range of about 7-8.5 ppm in H dimension, which proves formation of new IFN-gamma conformations. The addition to IFN-gamma of the activated-potentiated form of Ab to IFN-gamma also induced expansion of HSQC spectrum thus indicating alteration of molecule general alterations in the presence of RA dilutions of Ab to IFN-gamma. Adding of AC of Ab to IFN-gamma receptor as well as adding of placebo did not affect IFN-gamma conformation (these data are not reflected on the Figure)

| Sample | Number of related IFN-gamma peaks prior to adding of the corresponding test samples. | Number of related IFN-gamma peaks, which position in general spectrum did not change upon adding of the corresponding test samples. | Substance modifying potency in AU at C = 100 |
|---|---|---|---|
| IFN-gamma + AC of Ab to IFN-gamma | 128 | 117 | 8, 6 |
| IFN-gamma + AC of Ab to IFN-gamma receptor | 128 | 128 | — |
| IFN-gamma + AC of water | 128 | 128 | — |

The study results showed that only adding of activated-potentiated for of Ab to IFN-gamma affected IFN-gamma conformation. Solving Formula (1) taking C=100 and where A=128; $A_M$=113 provides:

$$X=100|128-113|/128$$

Thus, X=8.6 UA was

The results of Example 1 support the following conclusions:

1. Due to technique used for preparation of C12, C30, C50 homeopathic dilutions, an activated-potentiated form comprising a mixture of these three homeopathic dilutions a priori does not contain molecules of the starting substance;

2. Alterations of physical and chemical properties of IFN-gamma, the structure of which is similar to the structure of molecules of Ab to IFN-gamma, treated by the activated-potentiated form of Ab to IFN-gamma, present reliable evidence that the said activated-potentiated form is prepared on the basis of the starting substance IFN-gamma;

3. Alterations of physical and chemical properties of IFN-gamma treated by the activated-potentiated form of AB IFN-gamma, significantly validate the degree of modifying potency associated with activated-potentiated form and provides opportunity for expressing the modifying potency associated with the activated-potentiated carrier revealed by using NMR spectroscopy in dimensionless activity units as X=8.6 UA.

Example 2

Example 2 involves cysteine derivatization. Changes in conformation of IFN-gamma-R1, IFN-gamma-R2 in the presence of activated-potentiated form of Ab to IFN-gamma were assessed using biophysical probes. A simple and very specific way to introduce biophysical probes is through cysteine mutagenesis followed by reaction with derivatization reagents that carry the functional group to be investigated with the goal of probing its environment. The free sulfhydryl group of the cysteine is amenable for chemical derivatization with different reagents which can then be characterized by different spectroscopic methods. Here, the cysteine accessibility through absorbance measurements approach, were employed. Thus, the reaction rates between cysteines on IFN-gamma, IFN-gamma-R1 and IFN-gamma-R2 with a cysteine derivatization agent were quantified as indicators for conformation.

Testing of conformation of wild type IFN-gamma-R1 and IFN-gamma-R2 begins with step 1, which is preparation of 500 µl of IFN-gamma-R1, IFN-gamma-R2 solution eluted from the strep column with final concentration of IFN-gamma-R1, IFN-gamma-R2 obtained in the maximum concentration obtained from the elutions. Solution was prepared in buffer (2 mM sodium phosphate and 0.05% DM at pH6). Control testing involves with preparation 500 µl of buffer solution (2 mM sodium phosphate and 0.05% DM at pH6). Step 2 involves obtaining an absorbance spectrum. Step 3 is to add 4-PDS to all cuvettes from a 10 mM stock solution to yield a final concentration of 25 uM and mix it thoroughly. Step 4 is to record absorbance spectrum every 10 min until the absorbance peak at 323 nm is saturated. The difference spectra were obtained by subtracting the absorbance spectrum of protein alone in the presence and absence of 4-PDS to obtain change absorbance at 323 nm. The number of cysteines reacting with 4-PDS per molecule of IFN-gamma-R1 or IFN-gamma-R2 was not estimated due to the uncertainty in the amount of IFN-gamma-R1 or IFN-gamma-R2 present in the solution.

Testing of IFN-gamma effect on receptor conformation may now be performed. Step 1 involves sample testing, which begins with preparation 400 µl (PBS+0.05% DM+70 uM nonapeptide+25 uM 4-PDS)+50 µl IFN-gamma-R1 or IFN-gamma-R2+50 µl IFN-gamma (final concentration of 0.04 µg/µl), and control testing by which is prepared 450 µl (PBS+0.05% DM+70 uM nonapeptide+25 uM 4-PDS)+50 µl IFN-gamma-R1 or IFN-gamma-R2 and 450 1 (PBS+0.05% DM+70 uM nonapeptide+25 uM 4-PDS)+50 µl IFN-gamma (final concentration of 0.04 µg/µl). An absorbance spectrum is obtained in step 2. In step 3, 4-PDS is added to all cuvettes from a 10 mM stock solution to yield a final concentration of 25 µM and mix it thoroughly. Step 4 is recording of absorbance spectrum every 10 min until the absorbance peak at 323 nm is saturated.

Difference spectra were obtained by subtracting the absorbance spectrum of protein alone in the presence and absence of 4-PDS to obtain change absorbance at 323 nm. The number of cysteines reacting with 4-PDS per molecule of IFN-gamma-R1 or IFN-gamma-R2 was not estimated due to the uncertainty in the amount of IFN-gamma-R1 or IFN-gamma-R2 present in the solution.

Testing of activated-potentiated form of Abs to IFN-gamma effect on receptor conformation begins with step 1, confirmation of IFN-gamma-R1 or IFN-gamma-R2 by preparing 400 µl (PBS+0.05% DM+70 uM nonapeptide+25 uM 4-PDS)+50 µl IFN-gamma-R1+50 µl activated-potentiated form of Abs to IFN-gamma. For control, 450 µl (PBS+0.05% DM+70 uM nonapeptide+25 uM 4-PDS)+50 µl activated-potentiated form of Abs to IFN-gamma and 450 µl (PBS+0.05% DM+70 uM nonapeptide+25 uM 4-PDS)+50 µl IFN-gamma-R1 is prepared. In step 2 the components in an Eppendorf tube are pre-mixed before transfer to the cuvette. Step 3 is obtaining an absorbance spectrum. In step 3, 4-PDS is added to all cuvettes from a 10 mM stock solution to yield a final concentration of 25 µM and mixed thoroughly. Step 5 involves recording absorbance spectrum every 10 min until the absorbance peak at 323 nm is saturated.

Difference spectra were obtained by subtracting the absorbance spectrum of protein alone in the presence and absence of 4-PDS to obtain change absorbance at 323 nm. The number of cysteines reacting with 4-PDS per molecule of IFN-gamma-R1 or IFN-gamma-R2.

Figure 4:
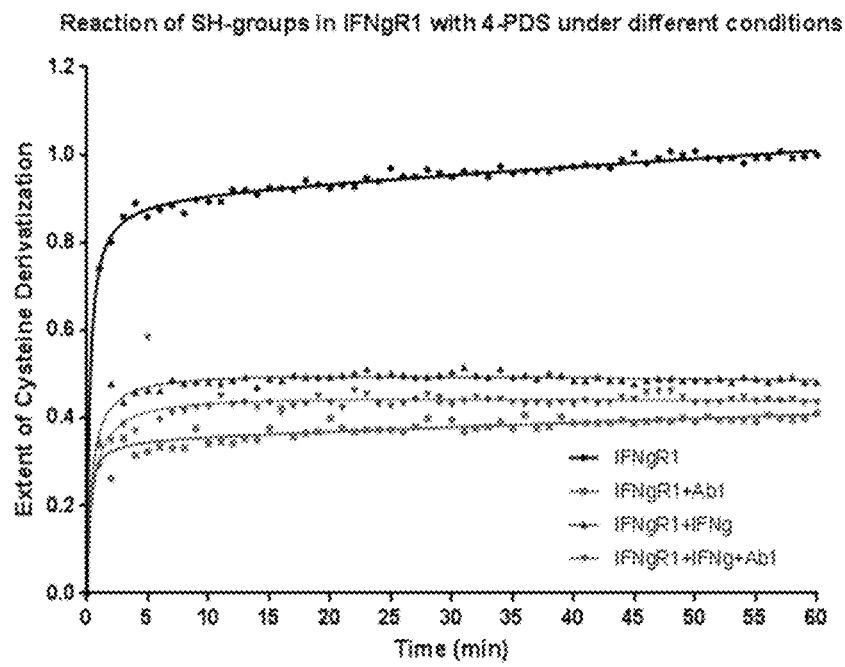
FIG. 4 is a time course of change at 323 nm for IFN-gamma-R1.
Figure 5:
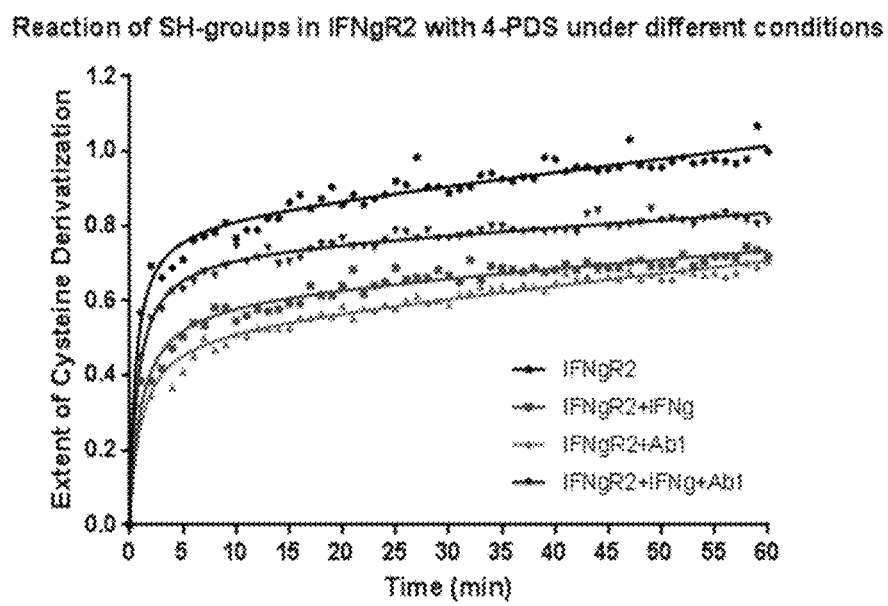
FIG. 5 is a time course of change at 323 nm for IFN-gamma-R2.

Results are represented on the FIGS. 4 and 5. Time course of change at 323 nm for IFN-gamma-R1 (FIG. 4), IFN-gamma-R2 (FIG. 5). Record absorbance spectrum every 10 min until the absorbance peak at 323 nm is saturated. Difference spectra are obtained by subtracting the absorbance spectrum either of IFN-gamma-Cys, IFN-gamma-R1, IFN-gamma-R2, or IFN-gamma, IFN-gamma-R1-Cys, IFN-gamma-R2, or IFN-gamma, IFN-gamma-R1, IFN-gamma-R2-Cys alone in the presence and absence of 4-PDS to obtain change absorbance at 323 nm. Ab1—is activated-potentiated form of Abs to IFN-gamma.

Thus, it was shown that activated-potentiated form of Abs to IFN-gamma yields a conformational change in the receptor complex, as evidenced by structural changes in conformational reporters attached to cysteines in the cytoplasmic domain of both IFN-gamma-R1 and IFN-gamma-R2, purified and solubilized in detergent micelles. Conformational changes in receptors were seen even in the absence of IFN-gamma, indicating activated-potentiated form of Abs to IFN-gamma have effects on its receptors directly.

Example 3

Example 3 involves a COX-1 enzyme assay. Example 3 tests the effect of pre-incubating the activated-potentiated form of Diclofenac with cyclooxygenase type 1 (COX-1) enzyme on the opportunity of Diclofenac to inhibit specific activity of the COX-1 enzyme. activated-potentiated form of distilled water was used as placebo.

A single concentration of each of the two test samples (activated-potentiated form of Diclofenac or placebo) was pre-incubated with the enzyme mixture at room temperature (RT) for 1 hour. After this, Diclofenac at the concentration $10^{-7}$ M ($IC_{50}$) was added to the pre-incubated enzyme and a second pre-incubation was performed for 5 minutes at RT. Then arachidonic acid was added to initiate the reaction, and the $OD_{590}$ was read after 5 minutes at RT and the optical density (OD) measured in a Perkin Elmer Victor 2 plate reader at 590 nm (please check the table 1).

TABLE 1

Schedule of the experiment.

| Number of wells replicas = 3 | Number of wells replicas = 3 |
|---|---|
| Test sample | Control # 1 |
| Stage 1. | Stage 1. |
| 130 µl of enzyme "Master Mix" (buffer, heme, enzyme - COX-1) + 20 µl of test sample | 130 µl of enzyme "Master Mix" (buffer, heme, enzyme - COX-1) + 20 µl of control |

Stage 2. Incubation at RT for 1 hour
Stage 3. 20 µl Diclofenac ($10^{-7}$M, $IC_{50}$) will be added to the well
Stage 4. Incubation at RT for 5 minutes
Stage 5. Add 20 µl of colorimetric substrate TMPD (N,N,N,'N'-tetramethyl-p-Phenylenediamine) kept on ice
Stage 6. Initiate reaction by addition of 10 µl of arachidonic acid kept on ice (50 uM final concentration)
Stage 7. Incubate for 3 min at RT and read at 590 nm (Perkin Elmer Victor II plate reader)

It was shown that pre-incubation of enzyme source (COX-1) with activated-potentiated form of Diclofenac for 1 hour prior to adding of Diclofenac and its subsequent incubation for 5 minute resulted in raising the Diclofenac inhibitory activity in comparison with placebo: 78% vs. 34%.

The description, examples and drawings contained herein represent the presently preferred embodiment of the invention and are, as such, a representative of the subject matter which is broadly contemplated by the present invention. The scope of the present invention fully encompasses other embodiments that may become obvious to those skilled in the art, and the scope of the present invention is accordingly limited by nothing other than the appended claims.

What is claimed is:

1. A method for quantitatively determining activity of activated-potentiated form of a substance, said method comprising:
   a. providing an activated potentiated form of a first substance,
   b. assuring absence of molecular form of the first substance in said activated-potentiated form,
   c. providing a molecular form of a second substance structurally similar to said first substance,
   d. measuring at least one physical, chemical or biological parameter (A) of said molecular form of second substance using a suitable analytical method,
   e. treating said molecular form of second substance with said activated-potentiated form, and
   f. measuring said at least one physical, chemical or biological parameter ($A_M$) of said treated molecular form of second substance using said analytical method, wherein said activity of said activated-potentiated form of said substance is the degree of difference between A and $A_M$,
   wherein the method further comprises of expressing activity of said activated-potentiated form of the first substance in relative units (X) in accordance with the formula X=C| A−$A_M$|/A;
   Wherein X is a number of activity units
   C is a dimensionless constant of proportionality that depends on the analytical method used;
   A is a value of a characteristic parameter of the second substance prior to its interaction with the said activated-potentiated form;
   $A_M$ is a value of the same characteristic parameter of the second substance after its interaction with the said activated potentiated form;
   and wherein the analytical method is selected from one of High Performance Liquid Chromatography, Enzyme Immune Assay Analysis, Nuclear Magnetic Resonance.

2. The method of claim 1, further comprising i) treating a molecular form of a different substance with said activated potentiated form of the first substance, ii) measuring said at least one physical, chemical or biological parameter (B) of said molecular form of said different substance using said analytical method, iii) measuring said at least one physical, chemical or biological parameter ($B_M$) of said treated molecular form of said different substance using said analytical method to determine specificity of said method, wherein said method is considered specific when said at least one physical, chemical or biological parameter changes in statistically significant manner for A− $A_M$ and does not change in statistically significant manner for B−$B_M$.

3. The method of claim 1, wherein said step of assuring absence of molecular form of the first substance comprises removing the molecular form of said first substance.

4. The method of claim 1, wherein said first substance is an antibody.

5. The method of claim 4, wherein said antibody is a polyclonal antibody.

6. The method of claim 1, wherein said first substance is a small organic molecule.

7. The method of claim 1, wherein said activated-potentiated form is a liquid.

8. The method of claim 1, wherein said activated-potentiated form of the first substance is impregnated onto a solid carrier.

9. The method of claim 1, wherein said second substance is a receptor for the first substance.

10. The method of claim 1, wherein said second substance is an antibody to the first substance.

11. The method of claim 1, wherein said first substance is an antibody to an antigen and said second substance is a receptor for said antigen.

12. The method of claim 1, wherein said first substance is an antibody to an antigen and said second substance is said antigen.

13. The method of claim 1, wherein said second substance is an enzyme catalyzed by the first substance.

* * * * *